(12) United States Patent
Hama et al.

(10) Patent No.: US 10,368,980 B2
(45) Date of Patent: Aug. 6, 2019

(54) MIDDLE EAR MUCOSA-LIKE CELL SHEET, PROCESS OF PRODUCING THE SAME AND METHOD OF USING THE SAME

(71) Applicants: Tokyo Women's Medical University, Tokyo (JP); The Jikei University, Tokyo (JP); CellSeed Inc., Tokyo (JP)

(72) Inventors: Takanori Hama, Tokyo (JP); Hiromi Kojima, Tokyo (JP); Hiroshi Moriyama, Tokyo (JP); Masayuki Yamato, Tokyo (JP); Teruo Okano, Tokyo (JP)

(73) Assignees: Tokyo Women's Medical University, Tokyo (JP); The Jikei University, Tokyo (JP); CellSeed Inc., Tokyo (JP)

(*) Notice: Subject to any disclaimer, the term of this patent is extended or adjusted under 35 U.S.C. 154(b) by 0 days.

(21) Appl. No.: 15/098,604

(22) Filed: Apr. 14, 2016

(65) Prior Publication Data
US 2016/0220356 A1 Aug. 4, 2016

Related U.S. Application Data

(62) Division of application No. 13/823,240, filed as application No. PCT/JP2011/071147 on Sep. 15, 2011, now abandoned.

(30) Foreign Application Priority Data

Sep. 15, 2010 (JP) .................................. 2010-226055

(51) Int. Cl.
*A61F 2/18* (2006.01)
*C12N 5/0793* (2010.01)
*A61L 27/38* (2006.01)
*A61K 35/12* (2015.01)

(52) U.S. Cl.
CPC ............ *A61F 2/18* (2013.01); *A61L 27/3804* (2013.01); *A61L 27/3813* (2013.01); *A61L 27/3839* (2013.01); *A61L 27/3886* (2013.01); *C12N 5/062* (2013.01); *A61F 2002/183* (2013.01); *A61F 2310/00365* (2013.01); *A61K 35/12* (2013.01); *A61L 2430/14* (2013.01); *C12N 2533/30* (2013.01)

(58) Field of Classification Search
None
See application file for complete search history.

(56) References Cited

U.S. PATENT DOCUMENTS

| | | | |
|---|---|---|---|
| 5,726,060 | A | 3/1998 | Bridges |
| 6,485,723 | B1 | 11/2002 | Badylak et al. |
| 2013/0289723 | A1 | 10/2013 | Hama et al. |

FOREIGN PATENT DOCUMENTS

| | | |
|---|---|---|
| JP | 2000-125863 A | 5/2000 |
| JP | 2003-513633 A | 4/2003 |
| JP | 2005-130838 A | 5/2005 |
| JP | 2007-222045 A | 9/2007 |
| WO | 01/32898 A2 | 5/2001 |
| WO | 2008/146997 A1 | 12/2008 |

OTHER PUBLICATIONS

J M Robinson, "Cholesteatoma: skin in the wrong place" J R Soc Med 1997;90:93-96.*
Aoki, Kazuhiro, M.D. et al., "Relationship Between Middle Ear Pressure, Mucosal Lesion, and Mastoid Pneumatization," *The Laryngoscope* (Dec. 1998), 108:1840-1845.
Kimura, Mototoshi, M.D., "Transplantation of the Mucosa of the Inferior Turbinate for Adhesive Otitis Media—Histomorphological Observation of Transplanted Mucosa of the Inferior Turbinate," *Jibiinkoka Tenbo* (Jun. 1991), 34(3):289-298. English Abstract.
Devalia et al., "Culture and comparison of human bronchial and nasal epithelial cells in vitro", Respiratory Medicine, 1990, vol. 84, pp. 303-312.
Bernd, "Epithelial Cells," 3 pages, available on Nov. 23, 2010.
Jorissen et al., "The preservation and regeneration of cilia on human nasal epithelial cells cultured in vitro," Arch Otorhinolaryngology, 1989, vol. 246, pp. 308-314.
Koo et al., "Airway Reconstruction With Carrier-Free Cell Sheets Composed of Autologous Nasal Squamous Epithelium," The Laryngoscope, Oct. 2007, vol. 117, pp. 1750-1755.
Reddy, Shashidhar S., Turbinate dysfunction: Focus on the role of the inferior turbinates in nasal airway obstruction, Turbinate Dysfunction, Mar. 2003, 11 pages.
Yamamoto et al., "Iiana Nenmaku Johi Saibo Sheet Ishoku ni yoru Chuji Nenmaku Saisei—Kato o Mochiita Ishoku Jikken," Otology Japan, Sep. 2009, vol. 19(4), pp. 623 (see concise explanation).
European Search Report, dated Dec. 22, 2014, EP Application No. 11825246.9, 6 pages.
Translation for JP 2005-130838, 33 pages, prepared Dec. 2014.
Translation for JP 200-125863, 43 pages, prepared Dec. 2014.
Sadé, Jacob, M.D. et al., "Middle Ear Gas Composition and Middle Ear Aeration," *Ann. Otol. Rhinol. Laryngol.* (1995) 104:369-373.
Nagase, Dai et al., "Histopathological Study of Transplanted Nasal Mucosa in Cases of Operative Ear with Adhesive Otitis Media," *Journal of the Showa Medical Association* (Apr. 28, 2003), 63(2):211-221.

(Continued)

*Primary Examiner* — Thane Underdahl
(74) *Attorney, Agent, or Firm* — Kilpatrick Townsend & Stockton LLP

(57) ABSTRACT

The purpose of the present invention is to obtain an alternative to a substitute of the mucosa in the middle ear which is engrafted on the surface of the bone in the middle ear, hyperplasia of the granulation tissue and the bone and the development of the fibroblast cells in the middle ear are suppressed, and to obtain a middle ear mucosa-like cell sheet retaining cilia in the surface layer, comprising culturing nasal epithelium cells on a cell culture substrate coated with a polymer whose hydration force changes within a temperature range of 0 to 80° C., wherein the cells are cultured within a temperature range where the hydration force of the polymer is weak, and then changing the temperature to a temperature at which the hydration force is strong to recover the cultured cell sheet.

16 Claims, 13 Drawing Sheets

(56) References Cited

OTHER PUBLICATIONS

Wada, Kota et al., "In vitro reconstruction of a three-dimensional middle ear mucosal organ and its in vivo transplantation," *Acta Oto-Latyngologica* (2006) 126:801-810.

Yaguchi, Yuichiro et al., "57 Middle Ear Mucosal Regeneration by Cell Sheet Prepared Using Temperature-Responsive Culture Dish," *Otology Japan* (2006), 16(4):297.

Yaguchi, Yuichiro et al., "Middle ear mucosa regeneration by grafting of artificial mucosa," *Acta Oto-Laryngologica* (2007), 127:1038-1044.

Yamamoto, Kazuhisa et al., "342 Middle Ear Mucosa Regeneration by Nasal Epithelial Cell Sheet Transplant—Transplant Tests Using Rabbit," *Otology Japan* (2009), 19(4):623.

International Search Report corresponding to PCT/JP2011/071147, dated Nov. 1, 2011, 3 pages.

Hirose et al, "Creation of Designed Shape Cell Sheets That Are Noninvasively Harvested and Moved onto Another Surface", Biomacromolecules, American Chemical Society, Oct. 1, 2000, vol. 1, No. 3, pp. 377-381.

\* cited by examiner

Fig.12
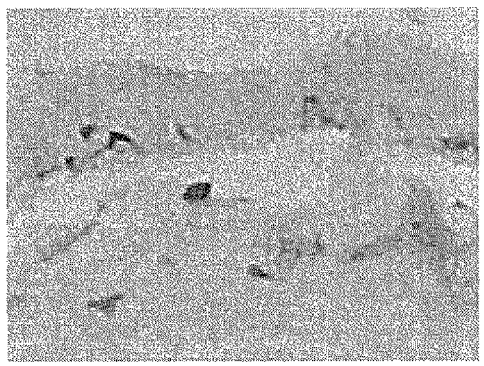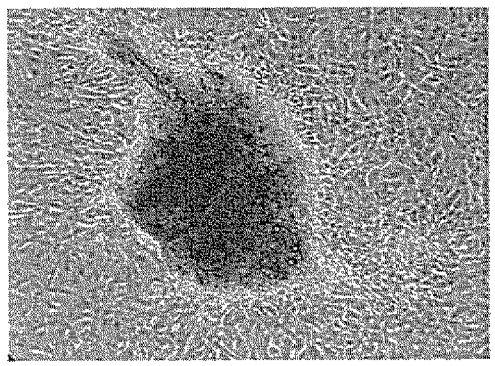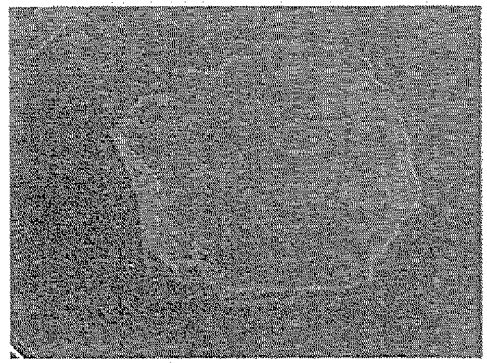

MIDDLE EAR MUCOSA-LIKE CELL SHEET, PROCESS OF PRODUCING THE SAME AND METHOD OF USING THE SAME

CROSS-REFERENCES TO RELATED APPLICATIONS

This application is a divisional of U.S. application Ser. No. 13/823,240 filed Jul. 18, 2013, which is national phase of International Application No. PCT/JP2011/071147 filed Sep. 15, 2011, which claims priority to Japanese Application No. 2010-226055, filed Sep. 15, 2010, which applications are incorporated herein by reference in their entirety for all purposes.

TECHNICAL FIELD

The present invention relates to a middle ear mucosa-like cell sheet useful in the field of medicine, biology, drug discovery, pharmacology, etc., a method for producing the same, and a method of use thereof. The present application claims priority to a Japanese application (Japanese Patent Application No. 2010-226055) filed on Sep. 15, 2010.

BACKGROUND ART

In surgeries of middle otitis including cholesteatoma in the field of otolaryngology, in cases where the mucosa can be preserved, recovery of physiological functions of the mucosa can be expected, and pneumatic space is assured in the middle ear cavity or the mastoid antrum after surgery. However, in many cases of cholesteatoma, it is difficult to preserve the mucosa in the mastoid antrum. Especially, in cases where a large area of the bone surface is exposed, it is highly probable that the formed eardrum is concaved again due to the occlusion of the isthmus of tympanum or due to the postoperative change of the drilled out mastoid antrum to form reconstitutive cholesteatoma (see Non-patent documents 1 and 2). Further, it is known that under such a diseased state, conversion of the mucosa to epithelium after surgery is delayed and the function of gas exchange through the mucosa and the function of the cilia are largely lost.

Accordingly, if the mucosa is regenerated on the surface of the bone exposed in a large area after surgery at an early stage, prevention of the re-adhesion of the eardrum and reconstitutive cholesteatoma is expected. In fact, although transplantation of nasal mucosa or oral mucosa, and use of collagen sponge have been studied, suturing in the narrow middle ear cavity is difficult, and it was found that the exposed bone surface is not appropriate as a scaffold of taking (see Non-patent documents 3 and 4). Further, there are many unclear points about the effect thereof.

Under the background, a novel cell culture method to detach cultured cell without being treated with a protease is described in Patent document 1, wherein cells are cultured at a temperature which below the upper limit or over the lower limit critical dissolution temperature, then the temperature is changed to a temperature which over the upper limit or below the lower limit critical dissolution temperature on the cell culture substrate which covered up its surface with a polymer of which the upper limit or lower limit critical dissolution temperature for water is within a temperature range of 0 to 80° C. Further, an detachment procedure for cultured skin cells with low damage is described in Patent document 2, wherein cells are cultured at a temperature below the upper limit or over the lower limit critical dissolution temperature, then the temperature is changed to a temperature over the upper limit or below the lower limit critical dissolution temperature by using the temperature-responsive cell culture substrate. It has been enabled to plan various new developments for conventional culturing technique by using the temperature-responsive cell culture substrate. As described in Patent document 3, if this technique will be developed more and use real cell existing in a liver tissue for a cell sheet, it is feasible that the sheet could maintain liver tissue cell function for a long term that is impossible by prior art.

However, there has been no discussion about nasal mucosa sheets with specific form.

If a mucosa can be reconstructed promptly on the surface of an exposed bone after the surgery in the operation of a middle otitis, an operative procedure of cholesteatoma of middle ear and adhesive otitis media may be changed. That is, if mucosa of mastoid antrum can be reconstructed after the surgery as expected, the mastoid antrum could be cavernous healing and we expect that plombage of mastoid antrum will be needless. On the other hand, when we think about clinical application to human, some problems surface. Further, there are some problems when a patient has advanced lesion, for example, tissue removal from a middle ear mucosa is difficult and it need preoperation to obtain the mucosa, in some cases, a mucosa from healthy tissue may be needed and ethical problem may also surface. However, nasal mucosa is easy to obtain in outpatient situation and it is preferably less burdens on patients.

CITATION LIST

Patent Documents

Patent Document 1: Japanese Unexamined Patent Publication (Kokai) No. 02-211865
Patent Document 2: Japanese Unexamined Patent Publication (Kokai) No. 05-192138
Patent Document 3: Japanese Unexamined Patent Re-publication (Saikohyo) No. 2007-080990

Non-Patent Documents

Non-patent document 1: Ann. Otol. Rhinol. Laryngol., 104, 369-373 (1995)
Non-patent document 2: Laryngoscope, 108, 1840-1845 (1998)
Non-patent document 3: Acta. Oto-Laryngologica., 127, 1038-1044 (2007)
Non-patent document 4: Acta. Oto-Laryngologica., 126, 801-810 (2006)

SUMMARY OF THE INVENTION

Technical Problem

Accordingly, an object of the present invention is to resolve above problems including postoperative problems of middle otitis. That is, this invention provide a novel middle ear mucosa-like cell sheet, a manufacturing method and an method of using the same, which are derived from ideas totally different from conventional arts.

Solution to Problem

To solve the above-described problems, the present inventors studied from various angles. As a result, the present inventors discovered that the middle ear mucosa-like cell sheet obtained by culturing the cells in the nasal mucosa tissue and reconstituting the cells into the form of a sheet is engrafted on the surface of the bone in the middle ear, hyperplasia of the granulation tissue and the bone and the development of the fibroblast cells in the middle ear are suppressed, so that the sheet can be used as a substitute of the mucosa in the middle ear lost by surgery of middle otitis or the like. The present inventors further discovered that the middle ear mucosa-like cell sheet of the present invention is useful as a substitute mucosa when the mucosa in the nasal cavity or oral cavity is lost. The present invention was completed based on these discoveries.

That is, the present invention provides a middle ear mucosa-like cell sheet retaining cilia in the surface layer. The present invention also provides a process of producing the middle ear mucosa-like cell sheet on the surface of a substrate coated with a temperature-responsive polymer. The present invention further provides a method of using the obtained middle ear mucosa-like cell sheet. The present inventors think that the present invention is a very important invention which was first realized using a cell structure, that is, a cell sheet, that was obtained by a novel concept unique in the world.

According to the present invention, a middle ear mucosa-like cell sheet comprising nasal epithelium cells retaining cilia thereof, wherein the middle ear mucosa-like cell sheet is detached from a culture substrate is provided. Examples of the middle ear mucosa-like cell sheet of the present invention include the following embodiment as a preferred embodiment, but are not limited thereto.

In one embodiment of the present invention, nasal epithelium cells to be used for a middle ear mucosa-like cell sheet of the present invention are originated from mucosa in nasal cavity, in paranasal sinus or in mastoid antrum. Preferably, the nasal epithelium cells are originated from superior turbinate mucosa, middle turbinate mucosa, inferior turbinate mucosa or mastoid antrum mucosa. More preferably, the nasal epithelium cells are originated from inferior turbinate mucosa.

In one embodiment of the present invention, the middle ear mucosa-like cell sheet of the present invention has a ventilatory function, a granulation tissue antiproliferative function and/or a mucin secretion function.

In one embodiment of the present invention, cells using for the middle ear mucosa-like cell sheet of the present invention is transgenic.

In one embodiment of the present invention, the middle ear mucosa-like cell sheet may be in the form of a laminate comprising two or more middle ear mucosa-like cell sheets. In another embodiment, the middle ear mucosa-like cell sheet may be in the form of a laminate comprising two or more middle ear mucosa-like cell sheets, wherein each middle ear mucosa-like cell sheet comprises one or more kinds of cells selected from vascular endothelial cell, endothelial precursor cell, fat-derived cell and mesenchymal stem cell.

According to the present invention, provided is a process of producing a middle ear mucosa-like cell sheet, comprising culturing nasal epithelium cells on a cell culture substrate coated with a polymer whose hydration force changes within a temperature range of 0 to 80° C., wherein the cells are cultured within a temperature range where the hydration force of the polymer is weak; and then changing the temperature to a temperature at which the hydration force is strong to detach the cultured middle ear mucosa-like cells while retaining the form of a sheet. Further, preferred embodiments of the middle ear mucosa-like cell sheet of the present invention include following embodiments, but not limited thereto.

In an embodiment of the present invention, the cell culture substrate is a cell insert which has a porous membrane for a cell culture surface.

An embodiment of the present invention comprises stacking the detached middle ear mucosa-like cell sheet on another middle ear mucosa-like cell sheet, or, optionally, repeating this operation, to stack the middle ear mucosa-like cell sheets. The middle ear mucosa-like cell sheet is one detached from the cell culture substrate without being treated with a protease. The middle ear mucosa-like cell sheet may be detached by intimately contacting the cultured cells with a carrier at the end of culturing, and detaching the cell sheet together with the carrier.

In an embodiment of the present invention, the middle ear mucosa-like cells may be collected from a living tissue. The number of the cells seeded in the culturing may be $3 \times 10^4$ to $2 \times 10^5$ cells/cm$^2$.

In an embodiment of the present invention, in the process of producing a middle ear mucosa-like cell sheet, the polymer whose hydration force changes within a temperature range of 0 to 80° C. is poly(N-isopropylacrylamide).

According to the present invention, provided is a method of using a middle ear mucosa-like cell sheet, comprising transplanting the middle ear mucosa-like cell sheet according to any one of claims 1 to 10 to a middle ear cavity or a mastoid antrum.

An embodiment of the present invention, a transplantation site may be preliminarily coated with a fibrin glue.

An embodiment of the present invention may be for treating cholesteatoma of middle ear, adhesive otitis, postoperative mucocele of paranasal sinus, frontal sinus cyst, oropharyngeal cancer, oropharyngeal cancer or paranasal cancer or laryngeal cancer, or reconstruction of middle ear cavity.

Advantageous Effects of Invention

The middle ear mucosa-like cell sheet illustrated by the present invention is engrafted on the surface of bone of the middle ear, and inhibits such as the hyperplasy of granulation tissue, the hyperplasy of bone, and the progression of fibroblast within middle ear cavity, and becomes an alternative of the mucosa of middle ear cavity which is lost by an operation such as otitis media. Also, this middle ear mucosa-like cell sheet becomes a useful mucosa when a membrane in nasal cavity or oral cavity is lost.

BRIEF DESCRIPTION OF DRAWINGS

FIG. 12 is a schematic diagram of the preparation of nasal mucosa cell sheet in Example 2.

DESCRIPTION OF EMBODIMENTS

Figure 1:
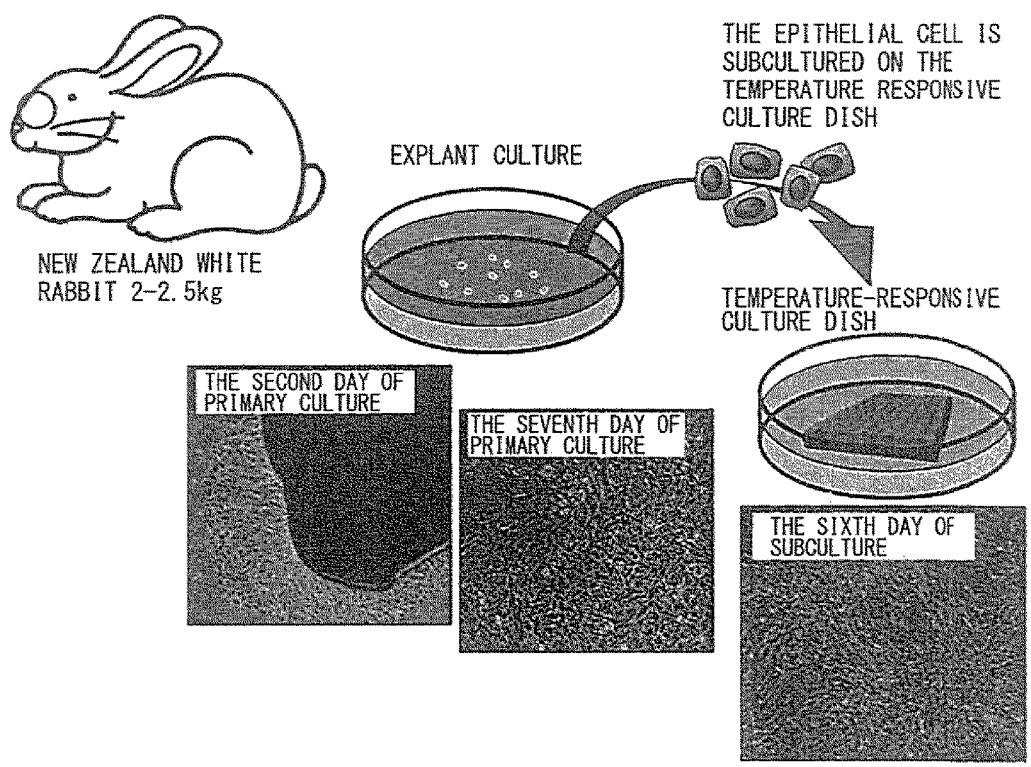
FIG. 1 is a schematic diagram of the preparation of nasal mucosa cell sheet in Example 1.

In the present invention, a middle ear mucosa-like cell sheet uses cells which retaining cilia on cell surface. The ciliate cells are preferable to account for more than 5%, preferably more than 8%, more preferably more than 10%, still more preferably more than 15%, most preferably more than 20% of whole cell to constitute the middle ear mucosa-like cell sheet of the present invention. If ciliate cells are account for less than 5%, a transplanted cell sheet may not produce an effect and is not preferable. A type of the cell is not particularly limited but representatives include a nasal epithelium cell. In that regard, it makes no difference for use when a nasal epithelium cells are originated from mucosa in nasal cavity, in nasal sinus or in mastoid antrum, but cells may be originated from superior turbinate mucosa, middle turbinate mucosa, inferior turbinate mucosa, mastoid antrum mucosa for example. Among them, inferior turbinate mucosa is particularly preferable as it is easy to collect. In the present invention, when nasal mucosa is used for material, which is abundant in living body and easy to collect as to be able to do in outpatient department, less burdens on patients and also ethical problem for patients may be avoided, which is preferred. Further, in the present invention, a surface of a cell has abundant cilia and preferable when using a nasal epithelium cell. Also, the present invention may include cells except mucosa cells, and it is not limited about a type of cells, but includes one or more kinds of cells selected from vascular endothelial cell, vascular endothelial precursor cell, fibroblast, marrow-derived cell, fat-derived cell, mesenchymal stem cell. Also, it is not limited about content ratio of these cells.

A cell using in the present invention including cells collected directly from living tissue, cells collected directly and differentiated by culture system or cell strains, but the type is not limited. The origin of the cells are not particularly limited, and examples thereof include human, rat, mouse, guinea pig, marmoset, rabbit, dog, cat, sheep, pig, goat, monkey or its immunocompromised animals, and in case of using a middle ear mucosa-like cell sheet of the present invention for treatment of human, we may preferably use cells originated from human, pig, monkey, chimpanzee. The present invention preferably uses a medium which usually used for cell culture, and it is not in particular a limited thing about using such a medium.

In the present invention, cells in mucosa in nasal cavity, nasal sinus, or mastoid antrum need to be treated by a specific process to make an individual state. The process includes a explant cultural method to seed tissues direct onto a culture substrate, a explant cultural method wherein a surface of a nasal mucosa epithelium tissue layer is detached physically from collected tissue and the epithelium tissue layer is seeded onto a culture substrate, a cultural method wherein collected tissue is treated by protease and the individual tissue is cultured, or combination of these methods according to the fixed method, and it is not limited. In the present invention, if gland tissues may be preliminary detached from collected nasal mucosa, a gland cell may not be mixed into the ultimately obtained nasal epithelium cell sheet, and a secretion by a gland cell may not cause, preferably. Inventors found it by energetic examination that human nasal mucosa epithelium tissue could be detached from human nasal mucosa, and it is extremely convenient when they carry out the present invention. Then a medium for this purpose may be performed according to a fixed method and it is not particularly limited, but includes KCM medium, DME medium, F-12 medium in case to use a nasal epithelium cells. At that time, an additive into the medium which is usually used for cell culture includes a cell culture for serum may be added. Also, to increase an adhesion of cells to surface of culture substrate for use, it may be coated by collagen, laminin, fibronectin, matrigel and the mixture of these as needed, and it is not particularly limited by these conditions in the present invention. In the present invention, the mucosa cell obtained in this way is seeded onto a temperature-responsive cell culture substrate which is a characteristic of the present invention as mention it later, then manufacture a cell sheet. At that time, the number of the cell sow in the culturing is preferably $3 \times 10^4$ to $2 \times 10^5$ cells/cm$^2$, more preferably $4 \times 10^4$ to $1.5 \times 10^5$ cells/cm$^2$, still more preferably $5 \times 10^4$ to $1 \times 10^5$ cells/cm$^2$. When dissemination density is less than $3 \times 10^4$ cells/cm$^2$, the hyperplasy rate of the mucosa cell is bad, and the expression degree of the function of produced middle ear mucosa-like cell sheet may be turned worse, and it is not preferable to perform the present invention. On the contrary, when seeded cell count is more than $2 \times 10^5$ cells/cm$^2$, the hyperplasy rate of the mucosa cell may be turned worse, and it is not preferable. A medium to use may be performed appropriately based on cells to use according to a fixed method, and it is not particularly limited, for example in case of the nasal epithelium cells include KCM medium, DMEM medium, F-12 medium, or mixture thereof. At that time, an additive into the medium which is usually used for cell culture such as the serum may be added. Inventors found it that when human nasal epithelium cells are cultured, regardless of a form of culture substrate as mention it later, if human serum is added, the cultured human nasal epithelium cells are grow well and as a result, a human nasal epithelium cell sheet having physical strength and flexibility could be produced. Further, if the serum use for it is an autologous serum from the patient whom the nasal mucosa tissue is collected, a human nasal epithelium cell sheet may increase more physical strength and flexibility and produce preferable condition for the present invention. At that time, serum concentration in medium for use is preferably 0.5-35%, preferably 1-20%, more preferably 5-15%, most preferably 8-12%. When serum concentration is less than 0.5% or more than 30%, strength of the cell on culturing may be weakend, and not preferable for the present invention. Further, to improve adherability of cell on surface of the culture substrate for use, it may be coated by collagen, laminin, fibronectin, matrigel and the mixture of these as needed, and it is not particularly limited by these conditions in the present invention.

In the present invention, the cells may be cultured at a temperature zone in which the hydration force of a polymer, of which hydration force varies in the temperature range of 0 to 80° C., is weak on a cell culture substrate the surface of which is coated with the polymer. Usually, the temperature may preferably be 37° C. which is a temperature for culturing cells. The temperature-responsive polymer for use in the present invention may be any of a homopolymer or copolymer. As such polymers, there can be mentioned polymers described in Japanese Unexamined Patent Publication (Kokai) No. 2-211865. Specifically, it can be obtained by monopolymerization or copolymerization of the following monomers. Monomers that can be used include, for example, a (meth)acrylamide compound, a N- (or N,N-di) alkyl-substituted (meth)acrylamide derivative, or a vinylether derivative, and in the case of a copolymer, any two or more of these can be used. Furthermore, a copolymer with monomers other than the above monomers, a graft polymer or copolymer with each other, or a mixture of polymers and copolymers can be used. Also, crosslinking can be performed as long as it does not impair the inherent property of the polymer. Since cells are cultured and detached at this time, and separation is carried out in the range of 5° C. to 50° C., temperature-responsive polymers include, but not limited to, poly-N-n-propyl acrylamide (the lower critical dissolution temperature of the monomer alone is 21° C.), poly-N-n-propyl methacrylamide (the lower critical dissolution temperature of the monomer alone is 27° C.), poly-N-isopropyl acrylamide (the lower critical dissolution temperature of the monomer alone is 32° C.), poly-N-isopropyl methacrylamide (the lower critical dissolution temperature of the monomer alone is 43° C.), poly-N-cyclopropyl acrylamide (the lower critical dissolution temperature of the monomer alone is 45° C.), poly-N-ethoxyethyl acrylamide (the lower critical dissolution temperature of the monomer alone is 35° C.), poly-N-ethoxyethyl methacrylamide (the lower critical dissolution temperature of the monomer alone is 45° C.), poly-N-tetrahydrofurfuryl acrylamide (the lower critical dissolution temperature of the monomer alone is 28° C.), poly-N-tetrahydrofurfuryl methacrylamide (the lower critical dissolution temperature of the monomer alone is 35° C.), poly-N,N-ethylmethyl acrylamide (the lower critical dissolution temperature of the monomer alone is 56° C.), poly-N,N-diethyl acrylamide (the lower critical dissolution temperature of the monomer alone is 32° C.), and the like. Monomers as used herein for copolymerization include, but not limited to, polyacrylamide, poly-N,N-diethyl acrylamide, poly-N,N-dimethyl acrylamide, polyethylene oxide, polyacrylic acid and a salt thereof, hydrated polymers such as polyhydroxyethyl methacrylate, polyhydroxyethyl acrylate, polyvinyl alcohol, polyvinyl pyrrolidone, cellulose, and carboxymethyl cellulose.

A method of coating the surface of the substrate with each of the above polymer as used in the present invention include, but not limited to, subjecting the substrate and the above monomer or polymer to an electron beam irradiation (EB), gamma-ray irradiation, ultraviolet ray irradiation, plasma treatment, corona treatment, and an organic polymerization reaction, or physical adsorption such as coating and kneading. The amount coated of a temperature-responsive polymer on the surface of the culture substrate may be in the range of 1.1-2.3 $\mu g/cm^2$, preferably 1.4-1.9 $\mu g/cm^2$, and more preferably 1.5-1.8 $\mu g/cm^2$. If the amount of coating is less than 1.1 $\mu g/cm^2$, the cells on the polymer cannot be easily detached even if stimulated, and inconveniently deteriorates work efficiency. Conversely, if the amount of coating exceeds 2.3 $\mu g/cm^2$, the cells cannot easily attach to the region, and thus the cells cannot be fully attached. In such a case, if a cell-adhering protein is further coated on the temperature-responsive polymer coating layer, the amount of the temperature-responsive polymer coating on the substrate surface may be 2.3 $\mu g/cm^2$ or more, and the amount coated of the temperature-responsive polymer may preferably be 9.0 $\mu g/cm^2$ or less, preferably 8.0 $\mu g/cm^2$ or less, and suitably 7.0 $\mu g/cm^2$ or less. When the amount coated of the temperature-responsive polymer is 9.0 $\mu g/cm^2$ or more, it makes the attachment of cells difficult even if a cell-adhering protein is further coated on the temperature-responsive polymer coating layer, and thus is not desirable. The type of such a cell-adhering protein includes, but not limited to, one type or a mixture of two types or more of, for example, collagen, laminin, laminin 5, fibronectin, matrigel, etc. The method for coating these cell-adhering proteins may follow any standard method, and usually a method of applying an aqueous solution of a cell-adhering protein to the substrate surface, and then removing the aqueous solution and rinsing is used. The present invention is a technology of using the cell sheet per se as much as possible using a temperature-responsive culture dish. Thus, an extremely large amount of a cell-adhering protein coated on the temperature-responsive polymer is not preferred. The measurement of the amount coated of a temperature-responsive polymer and the amount coated of a cell-attaching protein may follow any standard method, and there can be mentioned a method of measuring directly the cell-attached part using FT-IR-ATR, and a method of immobilizing a previously labelled polymer in a similar method and then estimating from the amount of the labelled polymer immobilized to the cell-attachment part, and any of the two methods can be used.

In the present invention, in order to detach and recover the cultured cell sheet from the temperature-responsive substrate, the temperature of the culture substrate to which the cultured cells are attached can be varied to higher than the upper critical dissolution temperature or lower than the lower critical dissolution temperature of the coating polymer on the culture substrate for detaching. At this time, this can be performed in the culture medium or in another isotonic solution, which can be selected depending on the purpose. In order to detach and recover more quickly and more efficiently, there can be used a method of lightly tapping or shaking the substrate and furthermore a method of stirring the culture medium using a pipet, alone or in combination. The culture conditions other than the temperature may follow any standard method, and is not specifically limited. For example, the medium used may be one to which a known serum such as fetal calf serum (FCS) has been added or a serum-free medium that contains no such serum.

The above will now be explained by taking poly(N-isopropylacrylamide) as an example of a temperature-responsive polymer. Poly(N-isopropylacrylamide) is known to be a polymer having a lower critical dissolution temperature of 31° C. Therefore, in a free state, the polymer chain dehydrates at a temperature of 31° C. or higher in water, thereby aggregating and becoming cloudy. Conversely, at a temperature of 31° C. or lower, the polymer chain hydrates and becomes dissolved in water. According to the present invention, this polymer has been coated and immobilized on the surface of the substrate such as a petri dish. Thus, at a temperature of 31° C. or higher, the polymer on the substrate surface may dehydrate, but since the polymer chain is coated and immobilized on the substrate surface, the substrate surface comes to exhibit hydrophobicity. Conversely, at a temperature of 31° C. or lower, the polymer on the substrate surface may hydrate, but since the polymer chain is coated and immobilized on the substrate surface, the substrate surface comes to exhibit hydrophilicity. The hydrophobic surface at this time is the surface suitable for cell's attachment and growth, and the hydrophilic surface becomes a surface to which cells cannot attach, and thus the cells in culture or the cell sheet can be easily detached only by cooling.

As a substrate that is coated, those commonly used in cell culture such as glass, reformed glass, polystyrene, a compound such as polymethylmethacrylate may be used, and a substance that can be shaped such as a polymer compound other than the above and ceramics can be used.

A form of the culture substrate in the present invention is not in particular a limited thing, but for example, there are dish, multi plate, flask, porous membrane, and also cell insert-like form in which cells are cultured on its porous membrane or flat membrane. Among them, when cells are cultured on porous membrane or on culture substrate with porous membrane in which the form like cell insert is used, the cell is cultured on porous membrane, accordingly, a medium is always produced through porous membrane during culturing, as a result, a ciliate cell used for the present invention may be stimulated its cilia and obtained cell sheet of the present invention may become physically strong and flexible cell sheet as it is preferable. At that time, it was find out that when the cell use for the present invention is an epithelium cell, the cell sheet is preferably multilayered and the obtained cell sheet may become physically stronger and more flexible cell sheet as it is preferable.

The middle ear mucosa-like cell sheet of the present invention is intact from damage by protein degradative protease represented by dispase, trypsin during culturing. Thus, therefore, a middle ear mucosa-like cell sheet detached from the substrate has an adhesive protein, and when detaching the mucosa cell to be sheet-like, it retains some degree of desmosome conformation between cells. By this conformation, it provides proper adhesion with affected tissue and effective performance of transplantation when transplants it. For dispase that is a proteolytic enzyme, it is generally known that a cell-cell desmosome structure can be detached while maintaining it for 10-40%. However, since most of the basal membrane-like proteins in between the cell-substrate are destroyed, the cell sheet obtained has a weak strength. In contrast, the cell sheet of the present invention maintains 60% or more of both of the desmosome structure and the basal membrane-like protein, and thus various effects mentioned above can be obtained.

Also, in a method of the present invention, when detach and collect a middle ear mucosa-like cell sheet from a culture substrate at the end of the culturing, a carrier may be closely-detached on a cultured cell and collected the middle ear mucosa-like cell sheet together with the carrier as needed. Typically, when detach and collect a cultured middle ear mucosa-like cell sheet from a temperature-responsive substrate at the end of the culturing, detach the carrier on the cultured cell, then change the temperature of coating a polymer on the culture substrate to set over the upper limit or below the lower limit critical dissolution temperature to be able to detach the middle ear mucosa-like cell sheet together with carrier. The carrier used as needed may include for example, hydrophilizated polyvinylidene fluoride (PVDF), polypropylene, polyethylene, cellulose and their derivatives, chitin, chitosan, collagen, papers like Japanese paper, urethane, netted or stocking netted high-a polymer material like spandex. In case if the carrier is netted or stocking netted high-a polymer material, it offer greater flexibility to a middle ear mucosa-like cell sheet, and a middle ear mucosa-like cell sheet may be produce which having a proper form for the transplantation site of middle ear cavity and mastoid antrum cavity.

A middle ear mucosa-like cell sheet of the present invention is originated from a cell retaining cilia. Therefore, the present invention has some characteristic function such as ventilatory function, gas exchange function by the cilia. That is, when the cell sheet of the present invention is transplanted into the middle ear cavity, nasal cavity and oral cavity, inside of the cavity can be ventilated by the cilia present in the cell sheet surface layer. A purpose of the present invention is to manufacture a cell sheet having such functions and to transplant in living body as to revitalize a vital function. On the other hand, when culturing ciliate cell, it is known that cilia on the cell surface are lost during a culturing process. In the present invention, it is not particularly limited, if even cilia are exist in the finally provided cell sheet, but when considering the final purpose of the present invention, more than 5%, preferably more than 8%, more preferably 10%, still more preferably 15%, most preferably more than 20% for a total cell count to constitute a cell sheet in which cilia may be existed in the cell. In general, a proportion of ciliate cell of mucosa tissue surface layer in middle ear cavity is considered to be about 10%, and it is preferable that the present invention is close to living tissue original state. In the present invention, ventilatory function and gas exchange function are regarded as synonymous, and all the function may be regarded as a function of cilia in cell surface layer. Also, middle ear mucosa-like cell sheet obtained by the present invention may secrete a specific substance such as mucin, hyaluronan and polysaccharide and a kind and volume of the substance is not particularly limited. Further, a cell sheet used for the present invention may be a transgenic to enhance the function of the cell sheet, and the method of transgenic may be on usual manner.

In the present invention, a middle ear mucosa-like cell sheet may be the form of a laminate including two or more middle ear mucosa-like cell sheets. The number of the laminates not particularly limited, but the stratifying number of times is preferably 10 times or less, preferably 5 times or less, more preferably 2 times or less. In case where a middle ear mucosa-like cell sheet is stratified, the cell density per single area of the sheet improves and preferably, the function as a middle ear mucosa-like cell sheet also improves. Further, middle ear mucosa-like cell sheet of the present invention, which is in the form of a laminate including two or more middle ear mucosa-like cell sheets, wherein each middle ear mucosa-like cell sheet includes one or more kinds of cells selected from vascular endothelial cell, endothelial precursor cell, fat-derived cell and mesenchymal stem cell in the range where the function of the present invention as described above is not impaired.

A method for fabricating a multilayered cell sheet of the present invention is not specifically limited, and the multilayered cell sheet can be obtained by detaching the cultured cells in a sheet-like form and layering the cultured cell sheets with each other using, as needed, a device for moving cultured cells. At this time, the temperature of the culture medium is not specifically limited, as long as it is lower than the upper critical dissolution temperature when the polymer coated on the surface of the culture substrate has the temperature, or higher than the temperature of the lower critical dissolution temperature when the polymer has the temperature. However, it is needless to say that a low temperature range in which cultured cells cannot grow or a high temperature range in which cultured cells die is obviously not suitable for culturing. Culture conditions other than the temperature may follow any standard method, and is not specifically limited. For example, the medium used may be one to which a known serum such as fetal calf serum (FCS) has been added or a serum-free medium that contains no such serum. Also, as needed, a device for moving a cell sheet can be used. Such a device is not specifically limited with regard to the material or shape, as long as it can capture the detached cell sheet. As such a material, generally, a material such as polyvinylidene difluoride (PVDF), silicone, polyvinyl alcohol, urethane, cellulose and a derivative thereof, chitin, chitosan, collagen, gelatin, or fibrin glue may be used in the form of a membrane, a porous membrane, an nonwoven fabric, or a woven fabric by being contacted with the cell sheet.

A middle ear mucosa-like cell sheet obtained from the present invention may be transplanted into a transplantation site in a living body. The transplantation site includes defective site in middle ear cavity, mastoid antrum, nasal cavity and oral cavity. Among them, the transplant to the defective mucosa in middle ear cavity may expect an effect of the present invention most and it is preferable. A transplantation site may be preliminarily neovascularized, and even if the site is applied an adhesive ingredient between the cells such as fibrin glue and collagen, it is not particularly limited. Also, a method of the neovascularization may not be particularly limited but including a method wherein embed the FGF which is a blood vessel growth factor in the micro-sphere, and effect on the living body for 8 to 10 days while changing the composition of the micro-sphere, size, an infusion range; a method wherein cut a polyethylene terephthalate mesh to any size and make a bag, and inject the FGF which dissolved in highly-concentrated agarose solution inside of the bag, then remove the bag 8 to 10 days later and make a space in which blood vessel is instructed.

A middle ear mucosa-like cell sheet which transplanted in the present invention retaining a basal membrane-like protein and its survival characteristics is quite preferable. At the time of the transplantation, the number of the cell count may change depending on a purpose, and when cells to transplant are sheet-like, the total activity of function in which the cell sheet retains by changing the size and form may change.

Further, when transplanting a middle ear mucosa-like cell sheet of the present invention, hyperplasy of granulation tissue, bone hyperplasy and further, extension of fibroblast at transplantation site may be inhibited. The mechanism has been analyzed at present, but as a result, it maintain a space retiring in cavity and suppress the narrowing of the space by transplantation of a middle ear mucosa-like cell sheet of the present invention.

By application of a middle ear mucosa-like cell sheet for human according to the present invention, treatment of cholesteatoma of middle ear, adhesive otitis, postoperative mucocele of paranasal sinus, frontal sinus cyst, oropharyngeal cancer, oropharyngeal cancer or paranasal cancer or laryngeal cancer, or reconstruction of middle ear cavity may be enable, but the purpose of the invention is not particularly limited thereto.

EXAMPLES

The present invention is described in detail below based on the examples without being limited thereby.

Example 1

A tissue fragment of rabbit nasal mucosa collected under the germfree condition was ex-planted onto a culture dish coated with type 1 collagen, and a primary culture was done with a KCM medium (Keratinocyte culture medium). Consequently, the nasal mucous epithelial cells crawled out of the surrounding area of the tissue fragment, and increased rapidly. Several days after the culture, the interfusion of the cells displaying the fibroblast cytoid form in part was observed. After culturing up to about 80% confluent, the nasal mucosa epithelial cells were recovered from the culture dish, and disseminated at a cell density of $5 \times 10^4$ cells/cm$^2$ onto the temperature-responsive culture dish (poly (N-isopropylacrylamide), coat volume 2.0 μg/cm$^2$) coated with collagen for tissue (CELLGEN). At that time, the temperature-responsive culture dish was obtained by applying 0.35 ml of N-isopropylacrylamide monomer dissolved in isopropyl alcohol at 35% onto the Falcon 3002 petri dish (6 cm diameter), then irradiating an electron ray of 0.25 MGy strength as it is, and coating with N-isopropylacrylamide monomer (PIPAAm) over the entire surface of culture dish. After the culture for six days, it was transferred to the $CO_2$ incubator at 20° C., and recovered successfully as the nasal mucosa cell sheet by performing low temperature treatment for 20 minutes. The process of operation is illustrated in FIG. 1.

Figure 2:
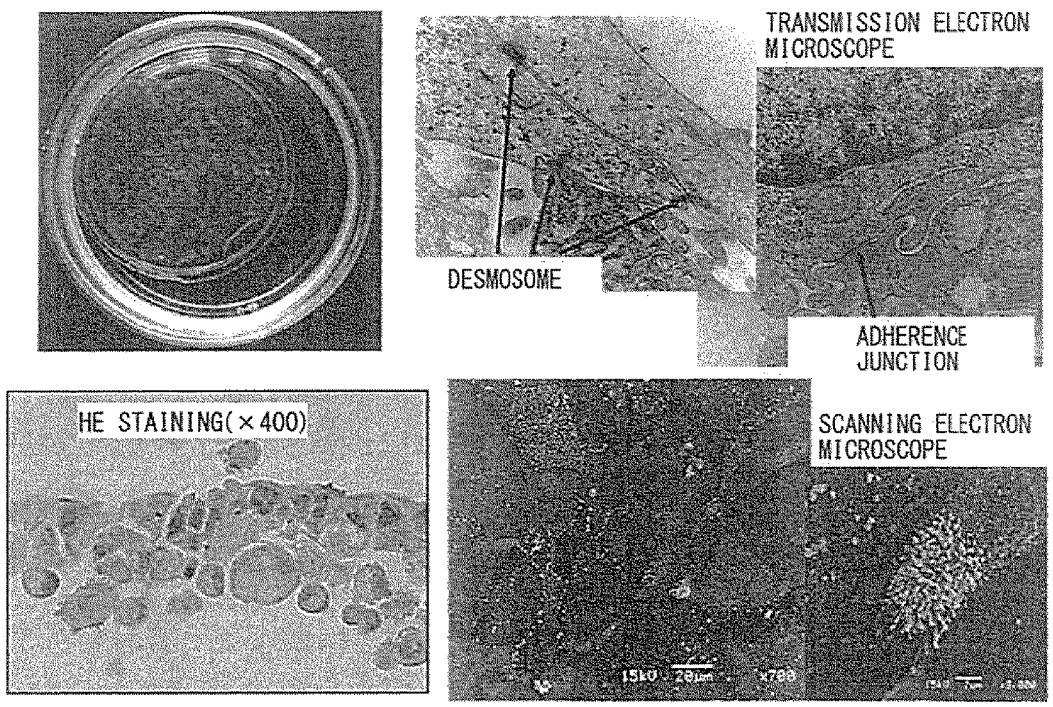
FIG. 2 illustrates the condition of nasal mucosa cell sheet obtained in Example 1.

When the manufactured nasal mucosa cell sheet was examined histologically by HE staining, it became obvious that epithelial cell like cells are arranged at one layer on the surface layer, and in the lower layer they have 3-dimensional structure consisted of some layer of fibroblast like cells. From the result of immunostaining, it was revealed that the cells arranged in single layer on this surface layer are Pan-CK positive epithelial cells, and are approximated very much to the normal mucosa tissue of middle ear consisted of the monolayer mucosa epithelium and the lower layer connective tissue, since the lower layer was composed of Vimentin positive fibroblasts. It is very interesting that in the process of subculture, the epithelial cell and the fibroblast respectively increased and segregated, and they had the same structure as a biological tissue. In addition, the ultrastructural observation of the cell sheet was done by using an electron microscope. From the observation of the surface layer of the nasal mucosa cell sheet by the scanning electron microscope (SEM), it was revealed that the hetero cells, such as the cells having countless microvilli on the cell surface and the cells having the cilia-like structure, are mixed. Also, from the result of observation by the transmission electron microscope (TEM), the structure of cell adhesion devices, such as the tight junction and the desmosome, the basement membrane-like structure in border of the epithelial layer and the fibroblast layer, and moreover, the deposition of ECM on the cell sheet undersurface which is important for an engraftment of the cell sheet were confirmed (FIG. 2).

Figure 3:
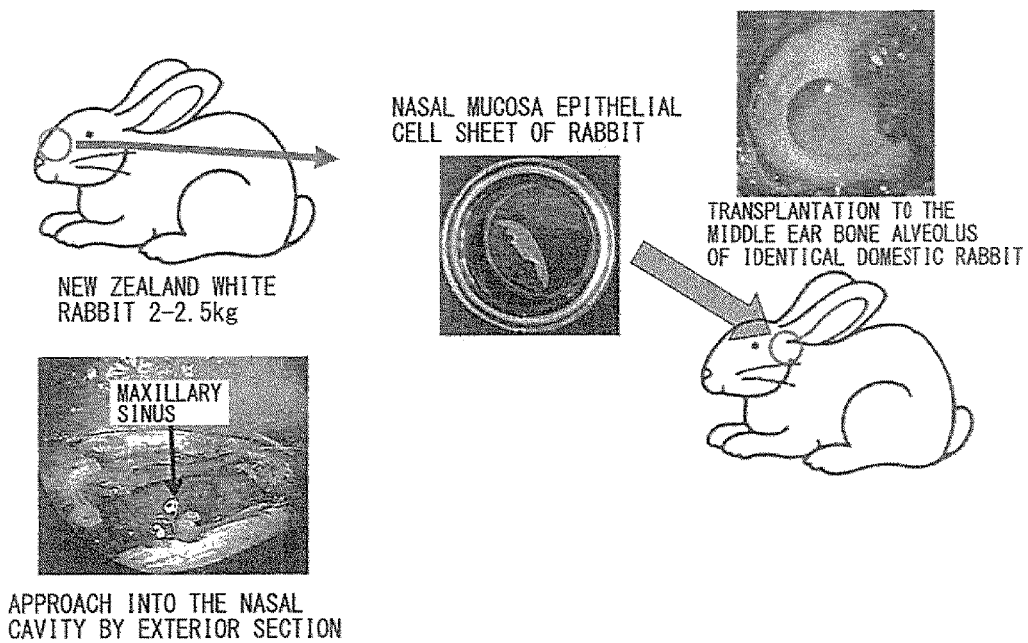
FIG. 3 is a schematic diagram of the transplantation of nasal mucosa cell sheet in Example 1.
Figure 4:
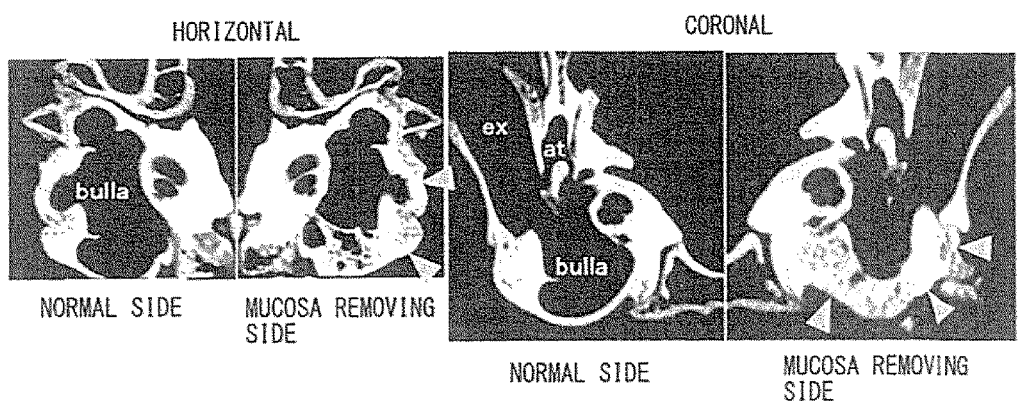
FIG. 4 illustrates the state of the hyperplasy of bone eight weeks after removing the mucosa of middle ear cavity in Example 1. X-ray CT (Latheta LCT-200) (ALOKA Co., Ltd.) was used for the imaging. ex: external acoustic meatus, bulla: middle ear bone alveolus, at: epitympanum.
Figure 5:
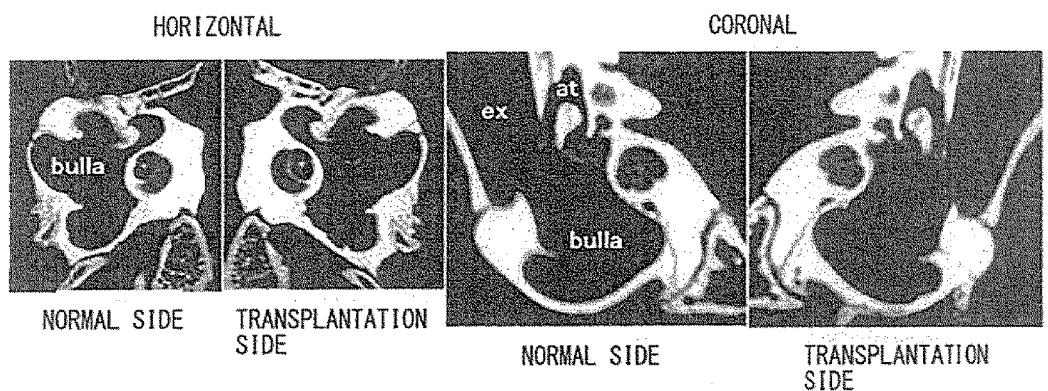
FIG. 5 illustrates the state of the hyperplasy of bone eight weeks after removing the mucosa of middle ear cavity and laying the nasal mucosa cell sheet of the present invention in Example 1. X-ray CT (Latheta LCT-200) (ALOKA Co., Ltd.) was used for the imaging. ex: external acoustic meatus, bulla: middle ear bone alveolus, at: epitympanum.
Figure 6:
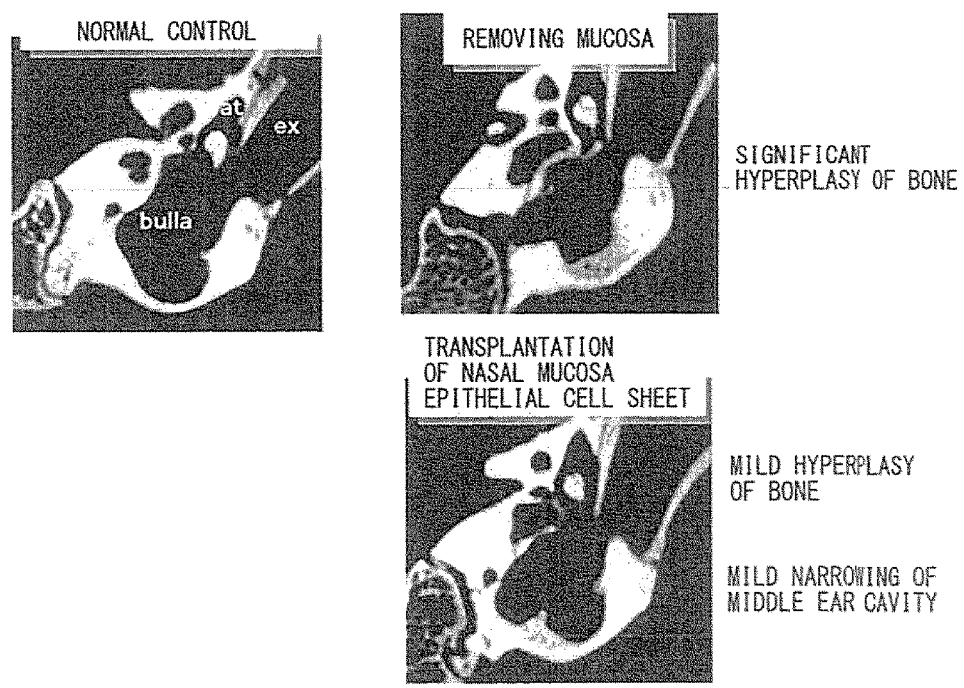
FIG. 6 illustrates the state of the hyperplasy of bone eight weeks after removing the mucosa of middle ear cavity and laying the nasal mucosa cell sheet of the present invention in Example 1. X-ray CT (Latheta LCT-200) (ALOKA Co., Ltd.) was used for the imaging. ex: external acoustic meatus, bulla: middle ear bone alveolus, at: epitympanum.
Figure 7:
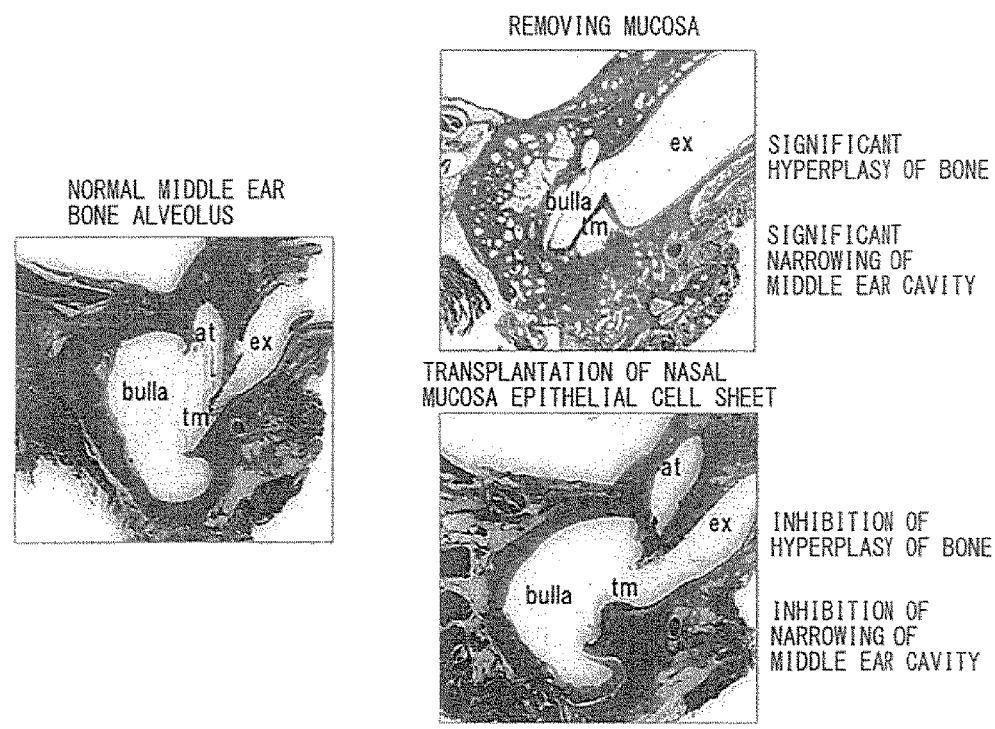
FIG. 7 illustrates the state of the hyperplasy of bone eight weeks after removing the mucosa of middle ear cavity and laying the nasal mucosa cell sheet of the present invention in Example 1. at: epitympanum, tm: tympanum, ex: external acoustic meatus, bulla: middle ear bone alveolus.
Figure 8:
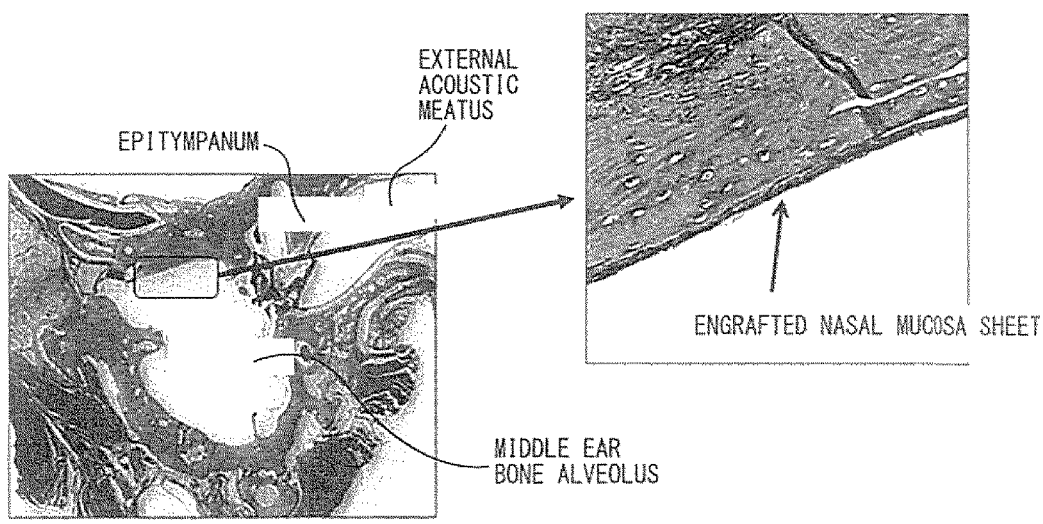
FIG. 8 illustrates the state of the surface of middle ear bone eight weeks after removing the mucosa of middle ear cavity and transplanting the nasal mucosa cell sheet of the present invention in Example 1.

The obtained nasal mucosa cell sheet was transplanted to the rabbit which was removed the mucosa of middle ear cavity in advance, and the effect of middle ear mucosa-like cell sheet of the present invention was confirmed. The process of operation at that time is illustrated in FIG. 3. Consequently, the narrowing in the middle ear cavity progressed and the obvious hyperplasy of bone was observed in the group which was removed the mucosa of middle ear cavity and then transplanted nothing (FIG. 4), however, the narrowing in the middle ear cavity did not progress and the hyperplasy of bone was not also observed in the group transplanted the middle ear mucosa-like cell sheet of the present invention (FIG. 5). This result was also found in the coronal CT (FIG. 6), or in the staining after collecting and making the decalcified section of the tissue of middle ear cavity (FIG. 7). In addition, from the analysis of the decalcifying section of transplanted region, it was observed that the engrafted nasal mucosa-like cell sheet remains (FIG. 8).

Figure 9:
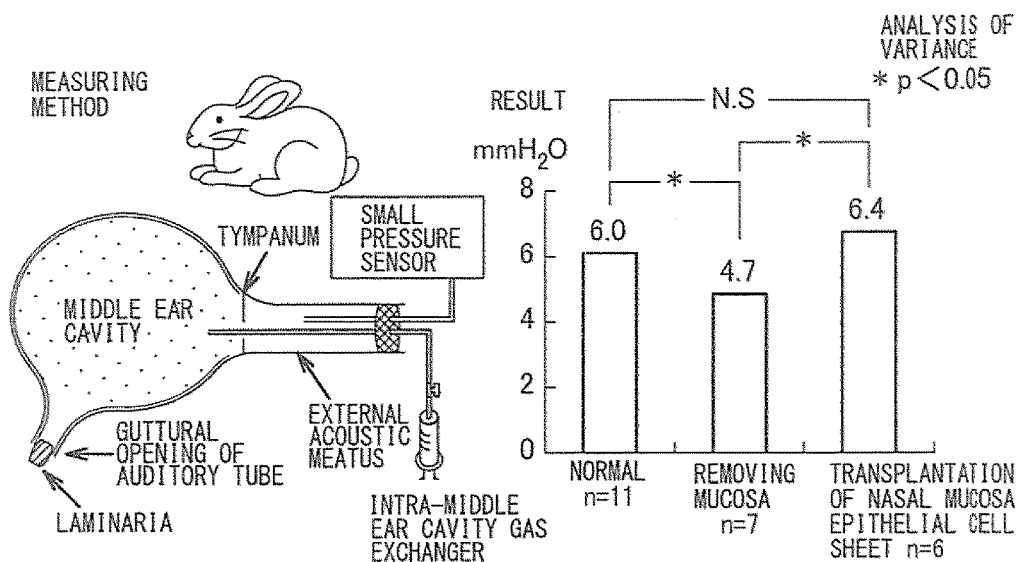
FIG. 9 illustrates the function of the middle ear cavity after the transplantation of the nasal mucosa cell sheet in Example 1.

For the evaluation of the function of the middle ear cavity which was transplanted the middle ear mucosa-like cell sheet of the present invention, as illustrated in FIG. 9, the middle ear cavity of rabbit was shut by plugging the portion of the auditory tube, the intra-middle ear cavity gas exchanger was inserted from the lateral part of the external acoustic meatus, and the function was measured by the small pressure sensor. Consequently, the measured value of the group transplanted the middle ear mucosa-like cell sheet of the present invention was better dominantly than that of the group removed the middle ear mucosa, and the value was almost close to a normal value. It is thought that the atmospheric pressure of the inside and outside of the tympanum is maintained at a state almost equal to normal tissue, and the optimal conductive function into inner ear can be maintained. Accordingly, it was confirmed that the middle ear mucosa-like cell sheet of the present invention is interchangeable with the middle ear mucosa.

Example 2

Figure 10:
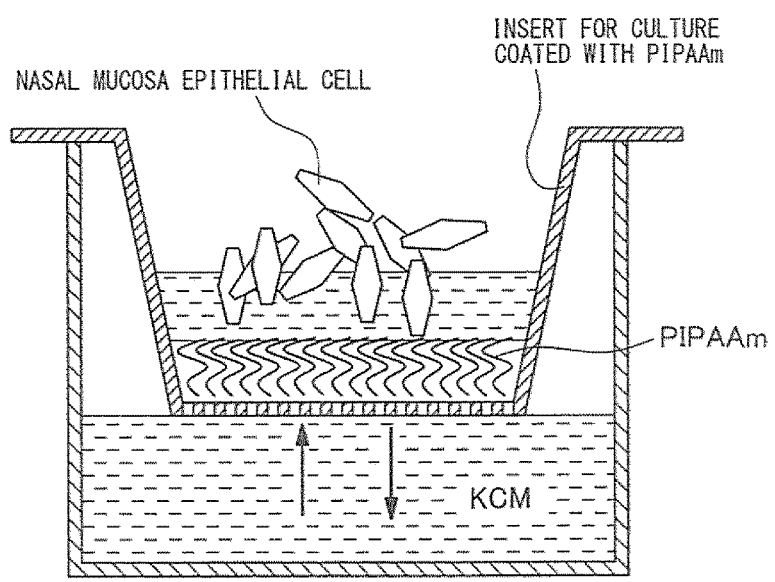
FIG. 10 is a schematic diagram of the preparation of nasal mucosa cell sheet in Example 2.
Figure 11:
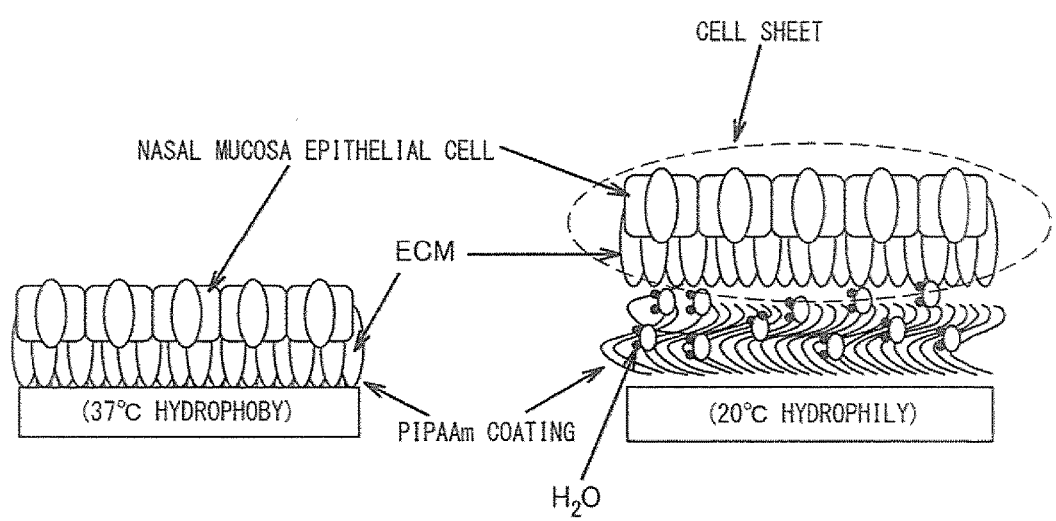
FIG. 11 is a schematic diagram of the preparation of nasal mucosa cell sheet in Example 2.
Figure 13:
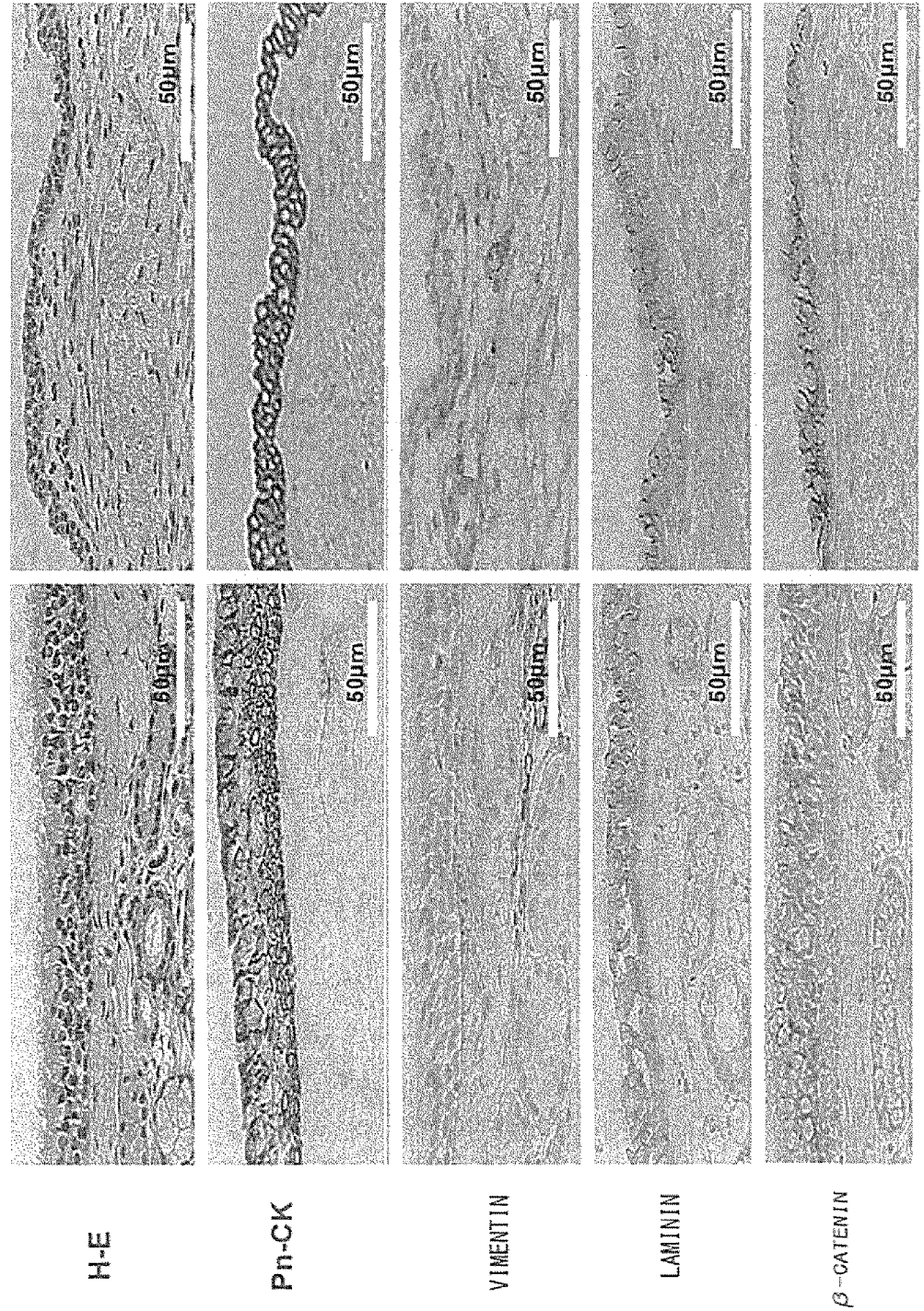
FIG. 13 is a diagram comparing the human mucosa tissue in Example 2.
Figure 14:
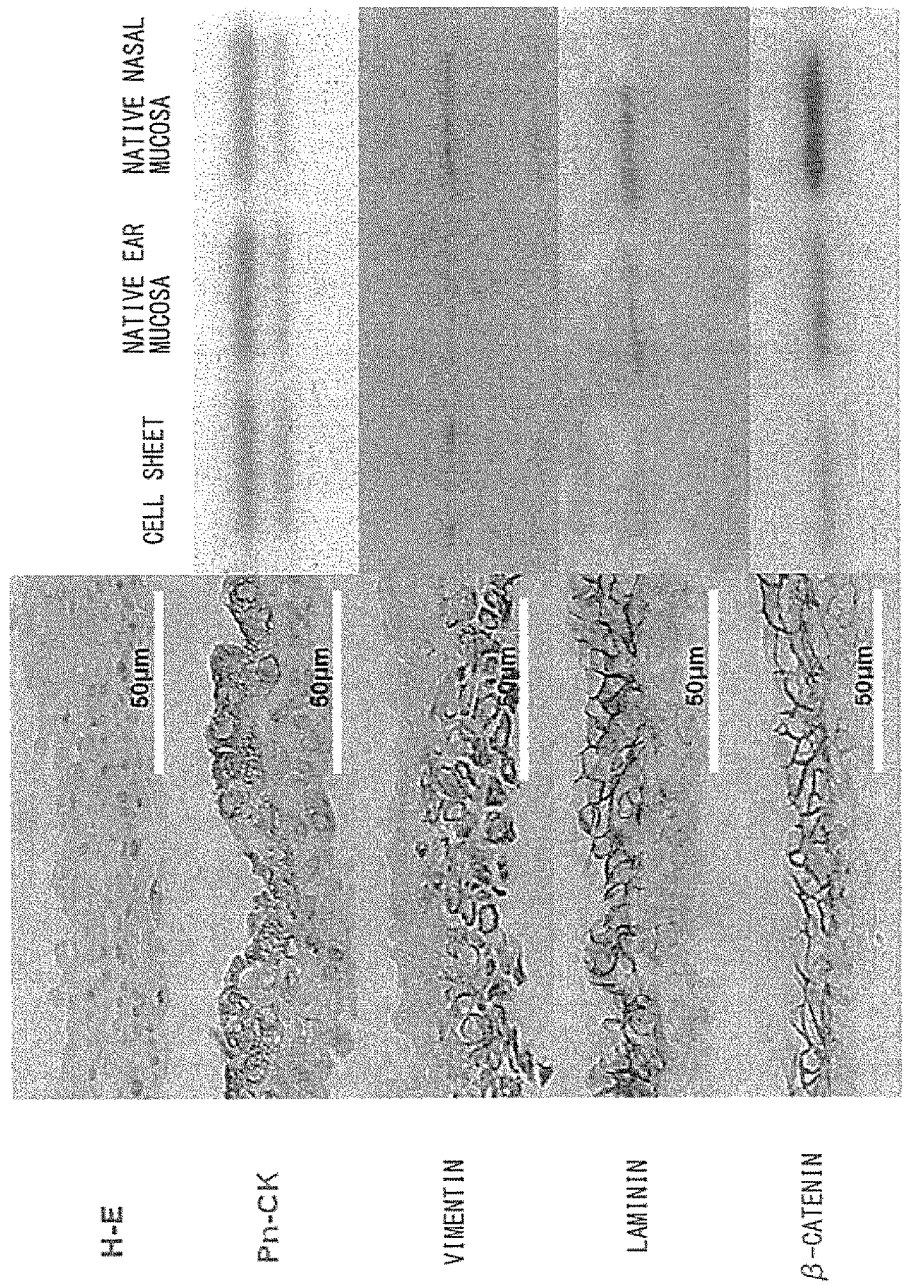
FIG. 14 is a diagram comparing the human mucosa with the nasal mucosa cell sheet in Example 2.
Figure 15:
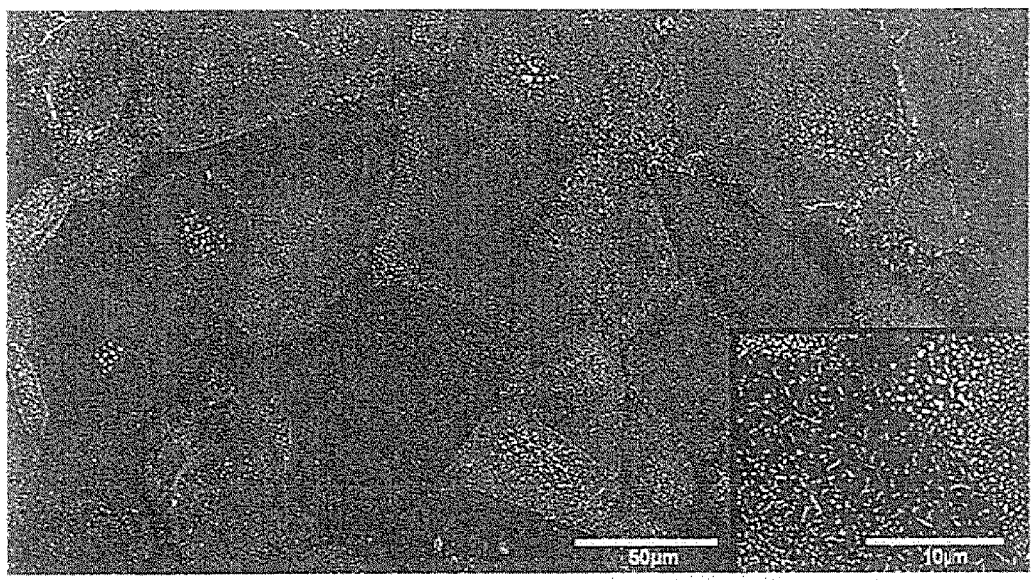
FIG. 15 illustrates the state of the human nasal mucosa cell sheet obtained in Example 2.
Figure 16:
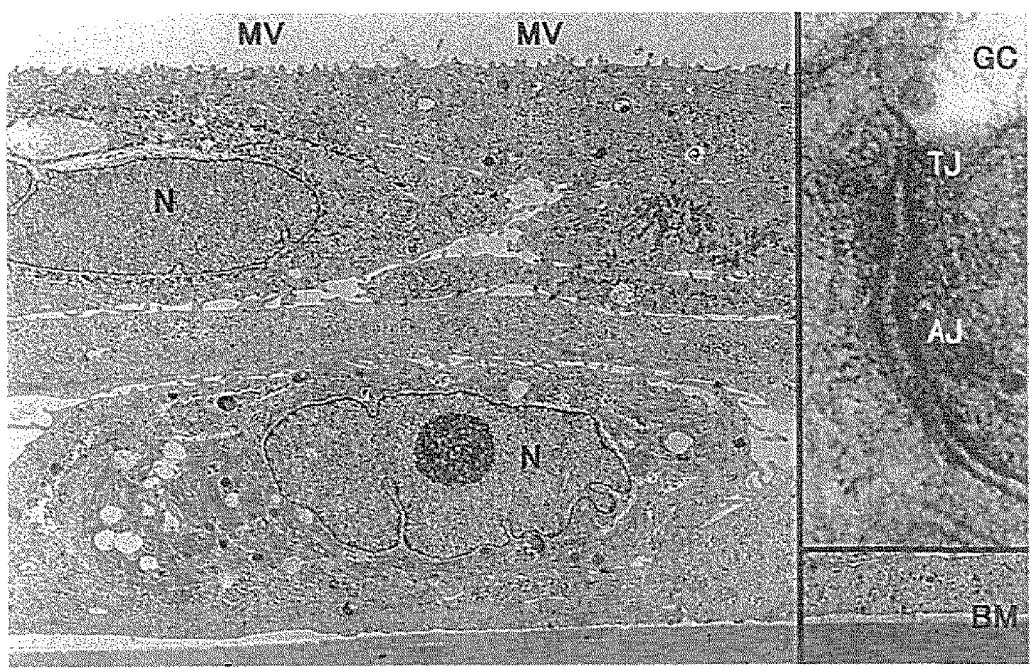
FIG. 16 illustrates the state of the human nasal mucosa cell sheet obtained in Example 2.

By the same method as Example 1, the section of inferior turbinate mucosa tissue in human nasal cavity (FIG. 12 upper left photograph) collected under the germfree condition was explanted on the culture dish coated with type I collagen, and a primary culture was done with KCM medium (Keratinocyte culture medium) (FIG. 12 lower left photograph). As illustrated in FIG. 10, the human nasal mucosa cell was disseminated on the cell insert whose porous membrane portion was coated with 1.5 µg/cm$^2$ volume of poly (N-isopropylacrylamide) by the same method as Example 1, and the obtained nasal mucosa cell was cultivated with the culture surface touched to air. After the culture for six days, it was transferred to the CO2 incubator at 20° C., and recovered successfully as the human nasal mucosa cell sheet by performing low temperature treatment for 20 minutes (FIG. 12 lower right photograph). The process of operation is illustrated in FIG. 11. Also, the situation of each process was illustrated in FIG. 12. In general, the middle ear mucosa is a part of the respiratory epithelium as well as the tracheal epithelium and the nasal mucosa epithelium, and it is known that the form of the mucosa epithelium is different in in the site within the middle ear cavity (FIG. 13 left column: the human normal nasal mucosa, FIG. 13 right column: the human normal middle ear mucosa). The site near an opening of auditory tube is abundantly covered with pseudostratified columnar epithelium including ciliated cell assuming the function of 5 egestion, but with the migrating to backward of middle ear cavity near tympanum, most part represents the form of flat epithelium of cell without cilia. This time, in the result of performing the morphological verification of the human middle ear mucosa and nasal mucosa, the nasal mucosa has subcutaneous grand tissue abundantly. However, it was proved that the expression forms of protein, such as cytokeratin, cadherin and catenin in epithelial cell, resemble greatly (FIG. 14). Therefore, it is considered to be possible enough to make the cell sheet similar to middle ear mucosa by recovering the epithelial cell of nasal mucosa. In addition, the ultrastructural observation of the human nasal mucosa cell sheet was performed by using an electron microscope. From the observation of the surface layer of the nasal mucosa cell sheet by the scanning electron microscope (SEM), it was revealed that the hetero cells, such as the cells having countless microvilli on the cell surface and the cells having the cilia-like structure, are mixed (FIG. 15). Also, from the result of observation by the transmission electron microscope (TEM), the structure of cell adhesion devices, such as the tight junction and the desmosome, the basement membrane-like structure in border of the epithelial layer and the fibroblast layer, and moreover, the deposition of ECM on the cell sheet undersurface which is important for an engraftment of the cell sheet were confirmed (FIG. 16).

Accordingly, the middle ear mucosa-like cell sheet of the present invention was obtained by using the temperature-responsive culture substrate. The obtained cell sheet was transplanted to rabbit, and the effect was examined. The obvious inhibition of the hyperplasy of bone and the narrowing in the middle ear cavity, was confirmed in the group of sheet transplantation. Then, in this time, for clinical application, the cell sheet using human cell was examined. And the cell sheet was able to be manufactured from inferior turbinate mucosa in human nasal cavity as well as animal model (ten examples conducted). Consequently, the middle ear mucosa-like cell sheet having the 3-dimensional structure approximated very much to middle ear mucosa tissue of living subject was successfully generated from the cell which was subcultured and grown from the mucosa tissue fragment collected from inferior turbinate mucosa in human nasal cavity. It required about 3 weeks from the collection of mucosa to the recovery of cell sheet. According to the examination of this time, the cell sheet using nasal mucosa cell was considered to be a useful graft material in the regeneration of mucosa after an operation of otitis media.

Example 3

Figure 17:
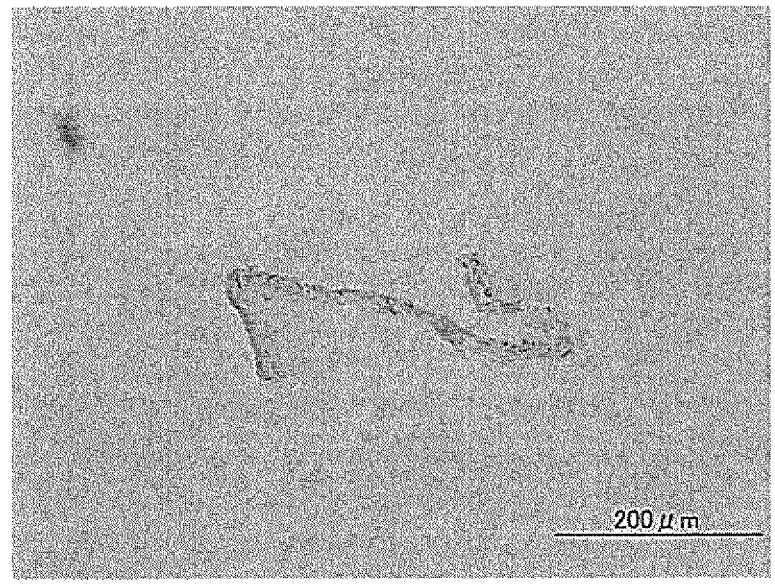
FIG. 17 illustrates the state of the epithelial tissue layer of human nasal mucosa obtained in Example 3.
Figure 18:
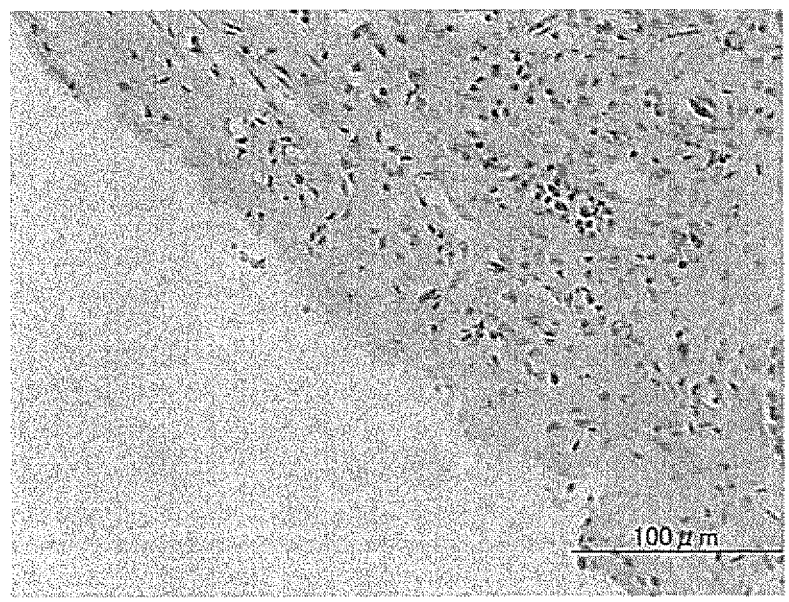
FIG. 18 illustrates the state of the other mucosa tissue detached the epithelial tissue layer of human nasal mucosa in Example 3.
Figure 19:
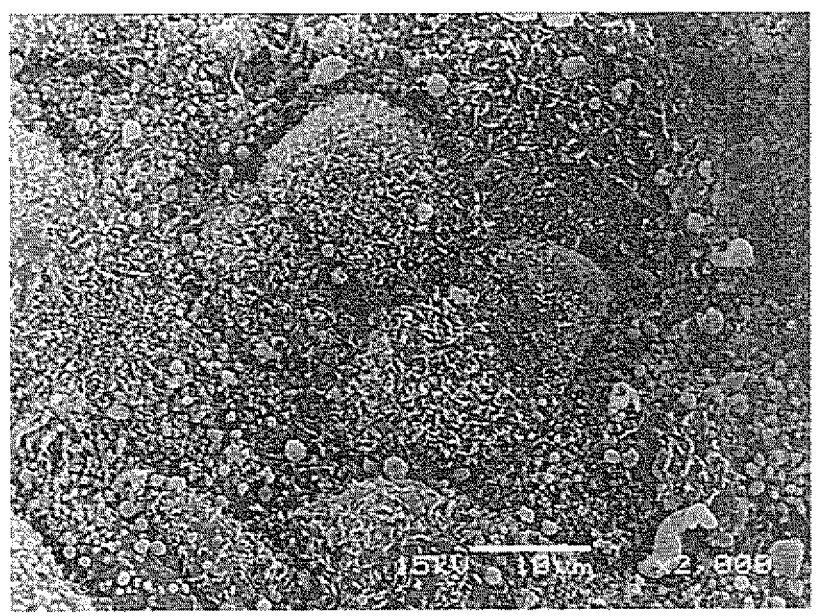
FIG. 19 illustrates the state of the human nasal mucosa cell sheet obtained in Example 3.
Figure 20:
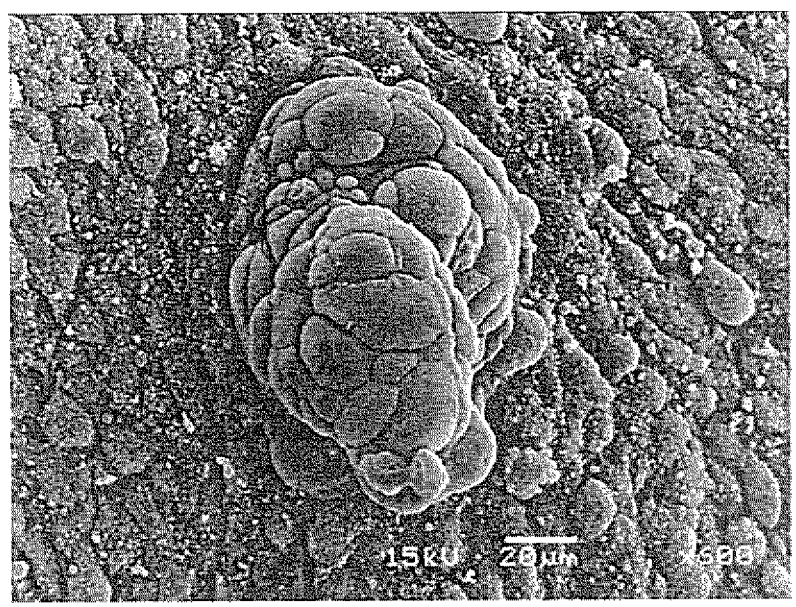
FIG. 20 illustrates the state of the human nasal mucosa cell sheet obtained in Example 3.

The portion of nasal mucosa epithelial tissue was detached from inferior turbinate mucosa tissue in human nasal cavity which was collected under the germfree condition, the nasal mucosa epithelial tissue was explanted on commercially-supplied culture dish, and the primary culture was done with KCM medium. The obtained nasal mucosa epithelial tissue is illustrated in FIG. 17, and the rest detached the nasal mucosa epithelial tissue is illustrated in FIG. 18. The human nasal mucosa cell was disseminated on the cell insert whose porous membrane portion was coated with 1.2 μg/cm² volume of poly (N-isopropylacrylamide) by the same method as Example 1, and cultivated with the culture surface touched to air. At that time, the KCM medium containing human serum 10% was utilized as a medium. After the culture for seven days, it was transferred to the $CO_2$ incubator at 20° C., and recovered successfully as the human nasal mucosa cell sheet by performing low temperature treatment for 20 minutes. The ultrastructural observation of the human nasal mucosa cell sheet was performed by using an electron microscope. From the observation of the surface layer of the nasal mucosa cell sheet by the scanning electron microscope (SEM), it was revealed that the nasal mucosa epithelial cell which was cultured on the cell insert with medium contained human serum as the present invention, promotes the increase of cilia of the cell surface, and has abundant microvilli on the cell surface (FIG. 19, FIG. 20).

Example 4

The human nasal mucosa cell sheet obtained in Example 3 was explanted to rabbit which was removed the mucosa of middle ear cavity in advance by the same method as Example 1. Consequently, the narrowing in the middle ear cavity did not progressed and the hyperplasy of bone was not also observed in the group transplanted the middle ear mucosa-like cell sheet of the present invention. According to the examination of this time, the cell sheet using nasal mucosa cell was considered to be a useful graft material in the regeneration of mucosa after an operation of otitis media, and the future clinical application as a novel postoperative therapeutic method leading significant change in operative procedure for the cholesteatoma of the middle ear and adhesive otitis media is expected.

INDUSTRIAL APPLICABILITY

The middle ear mucosa-like cell sheet manufactured on the temperature-responsive culture substrate is engrafted on the surface of bone of the middle ear, and inhibits such as the hyperplasy of granulation tissue, the hyperplasy of bone and the progression of fibroblast within middle ear cavity, and becomes an alternative of the mucosa of middle ear cavity which is lost by an operation such as otitis media. Also, this middle ear mucosa-like cell sheet becomes a useful mucosa when a membrane in nasal cavity or oral cavity is lost.

We claim:

1. A method of transplanting a middle ear mucosa-like cell sheet into a subject in need thereof, the method comprising
    (i) preparing a middle ear mucosa-like cell sheet containing nasal epithelium cells retaining cilia thereof and nasal mucosa cells, the nasal epithelium cells originating from inferior turbinate mucosa, middle turbinate mucosa, or mucosa in paranasal sinus, wherein the nasal epithelium cells in the middle ear mucosa-like cell sheet comprise flat forms of the nasal epithelium cells, said preparing including:
        a) detaching a portion of nasal mucosa epithelial tissue from inferior turbinate mucosa, middle turbinate mucosa, or mucosa in paranasal sinus while excluding gland cells;
        b) explanting the portion of nasal mucosa epithelial tissue on a cell culture substrate to cause proliferation of mucosal cells from the portion of nasal mucosa epithelial tissue, wherein the cell culture substrate is coated with a cell-adhering protein;
        c) culturing the proliferated mucosal cells on a cell insert coated with a polymer which exhibits a weaker hydration force in a first temperature range than in a second temperature range, said culturing being carried out within the first temperature range such that the cultured middle ear mucosa-like cells form a sheet on the cell insert;
        d) changing the temperature from within the first temperature range to the second temperature range to thereby detach the sheet of cultured middle ear mucosa-like cells from the cell insert while retaining the form of the sheet; and
    (ii) transplanting the middle ear mucosa-like cell sheet to a middle ear cavity or a mastoid antrum of a subject.

2. The method of claim 1, wherein the middle ear mucosa-like cell sheet is transplanted to a transplantation site preliminarily coated with a fibrin glue.

3. The method of claim 1, wherein the subject is in need of treatment for cholesteatoma of middle ear, adhesive otitis, postoperative mucocele of paranasal sinus, frontal sinus cyst, oropharyngeal cancer, oropharyngeal cancer, paranasal cancer or laryngeal cancer, or reconstruction of a middle ear cavity.

4. The method of claim 1, wherein the detached the middle ear mucosa-like cell sheet comprises an adhesive protein that is intact and was not damaged by a protease.

5. The method of claim 1, wherein the middle ear mucosa-like cell sheet is multilayered.

6. The method of claim 1, wherein the middle ear mucosa-like cell sheet has a ventilatory function.

7. The method of claim 1, wherein the middle ear mucosa-like cell sheet has a granulation tissue inhibitory function.

8. The method of claim 1, wherein the middle ear mucosa-like cell sheet has a mucin secretion function.

9. The method of claim 1, wherein the middle ear mucosa-like cell sheet is transgenic.

10. The method of claim 1, wherein the middle ear mucosa-like cell sheet further comprises one or more types of cells selected from the group consisting of vascular endothelial cells, an endothelial precursor cell, fat-derived cells, and mesenchymal stem cells.

11. The method of claim 1, wherein the middle ear mucosa-like cell sheet further comprises two or more middle ear mucosa-like cell layers, wherein each of the middle ear mucosa-like cell layers comprises one or more types of cells selected from the group consisting of vascular endothelial cells, an endothelial precursor cells, fat-derived cells, and mesenchymal stem cells.

12. A method of preparing a middle ear mucosa-like cell sheet containing nasal epithelium cells to be transplanted into a subject in need thereof, the middle ear mucosa-like cell sheet containing nasal epithelium cells retaining cilia thereof and nasal mucosa cells, the nasal epithelium cells originating from inferior turbinate mucosa, middle turbinate mucosa, or mucosa in paranasal sinus, wherein the nasal epithelium cells in the middle ear mucosa-like cell sheet comprise flat forms of the nasal epithelium cells, said method comprising:
    a) detaching a portion of nasal mucosa epithelial tissue from inferior turbinate mucosa, middle turbinate mucosa, or mucosa in paranasal sinus while excluding gland cells,
    b) explanting the portion of nasal mucosa epithelial tissue on a cell culture substrate to cause proliferation of mucosal cells from the portion of nasal mucosa epithelial tissue, wherein the cell culture substrate is coated with a cell-adhering protein, c) culturing the proliferated mucosal cells on a cell insert coated with a polymer which exhibits a weaker hydration force in a first temperature range than in a second temperature range, said culturing being carried out within the first temperature range such that the cultured middle ear mucosa-like cells form a sheet on the cell insert, and d) changing the temperature from within the first temperature range to the second temperature range to thereby detach the sheet of cultured middle ear mucosa-like cells from the cell insert while retaining the form of the sheet.

13. The method of claim 1, wherein the cell-adhering protein is one or more cell-adhering protein(s) selected from a group consisting of collagen, laminin, laminin 5, fibronectin and matrigel.

14. The method of claim 1, wherein the cell-adhering protein is collagen.

15. The method of claim 12, wherein the cell-adhering protein is one or more cell-adhering protein(s) selected from a group consisting of collagen, laminin, laminin 5, fibronectin and matrigel.

16. The method of claim 12, wherein the cell-adhering protein is collagen.

* * * * *